(12) United States Patent
Vilsmeier et al.

(10) Patent No.: US 7,744,605 B2
(45) Date of Patent: Jun. 29, 2010

(54) MEDICAL INSTRUMENT WITH A TOUCH-SENSITIVE TIP

(75) Inventors: Stefan Vilsmeier, Kufstein (AT); Michael Bertram, Markt Schwaben (DE); Rainer Birkenbach, Poing (DE)

(73) Assignee: BrainLAB AG, Feldkirchen (DE)

( * ) Notice: Subject to any disclaimer, the term of this patent is extended or adjusted under 35 U.S.C. 154(b) by 2215 days.

(21) Appl. No.: 10/134,974

(22) Filed: Apr. 29, 2002

(65) Prior Publication Data

US 2003/0069588 A1  Apr. 10, 2003

(30) Foreign Application Priority Data

Oct. 10, 2001  (EP)  .................... 01123369

(51) Int. Cl.
*A61B 19/00* (2006.01)
(52) U.S. Cl. ..................................... 606/130
(58) Field of Classification Search ................. 600/407, 600/409, 415, 417, 427; 606/130, 116; 33/561
See application file for complete search history.

(56) References Cited

U.S. PATENT DOCUMENTS

| | | | |
|---|---|---|---|
| 4,279,080 A * | 7/1981 | Nakaya ....................... 33/561 |
| 4,399,823 A | 8/1983 | Donnelly |
| 4,982,611 A * | 1/1991 | Lorenz et al. ........... 73/862.043 |
| 5,339,799 A | 8/1994 | Kami et al. |
| 5,676,673 A * | 10/1997 | Ferre et al. ................... 606/130 |
| 5,718,228 A | 2/1998 | Hiruta et al. |
| 6,006,126 A | 12/1999 | Cosman |
| 6,132,368 A * | 10/2000 | Cooper ....................... 600/102 |
| 6,235,038 B1 * | 5/2001 | Hunter et al. ............... 606/130 |
| 6,381,485 B1 * | 4/2002 | Hunter et al. ............... 600/407 |
| 6,499,488 B1 * | 12/2002 | Hunter et al. ............... 128/899 |
| 2004/0059328 A1 * | 3/2004 | Daniel et al. ................... 606/41 |

FOREIGN PATENT DOCUMENTS

| | | |
|---|---|---|
| EP | 0 000 556 | 2/1979 |
| WO | 99/38449 | 8/1999 |
| WO | 00/78209 | 12/2000 |

* cited by examiner

*Primary Examiner*—Anhtuan T Nguyen
*Assistant Examiner*—Tuan V Nguyen
(74) *Attorney, Agent, or Firm*—Renner, Otto, Boisselle & Sklar, LLP

(57) ABSTRACT

The invention relates to a medical instrument comprising an instrument body (8), an instrument tip (5) and a tracking means (1,2, 4), characterized in that said instrument tip (5) is fitted with a touch-sensor (3) which detects a contact between said tip (5) and an object, for example a patient. It is preferably realized as an indicator device or pointer, in particular as a registering pointer for instrument tracking systems.

11 Claims, 1 Drawing Sheet

MEDICAL INSTRUMENT WITH A TOUCH-SENSITIVE TIP

Figure 1:
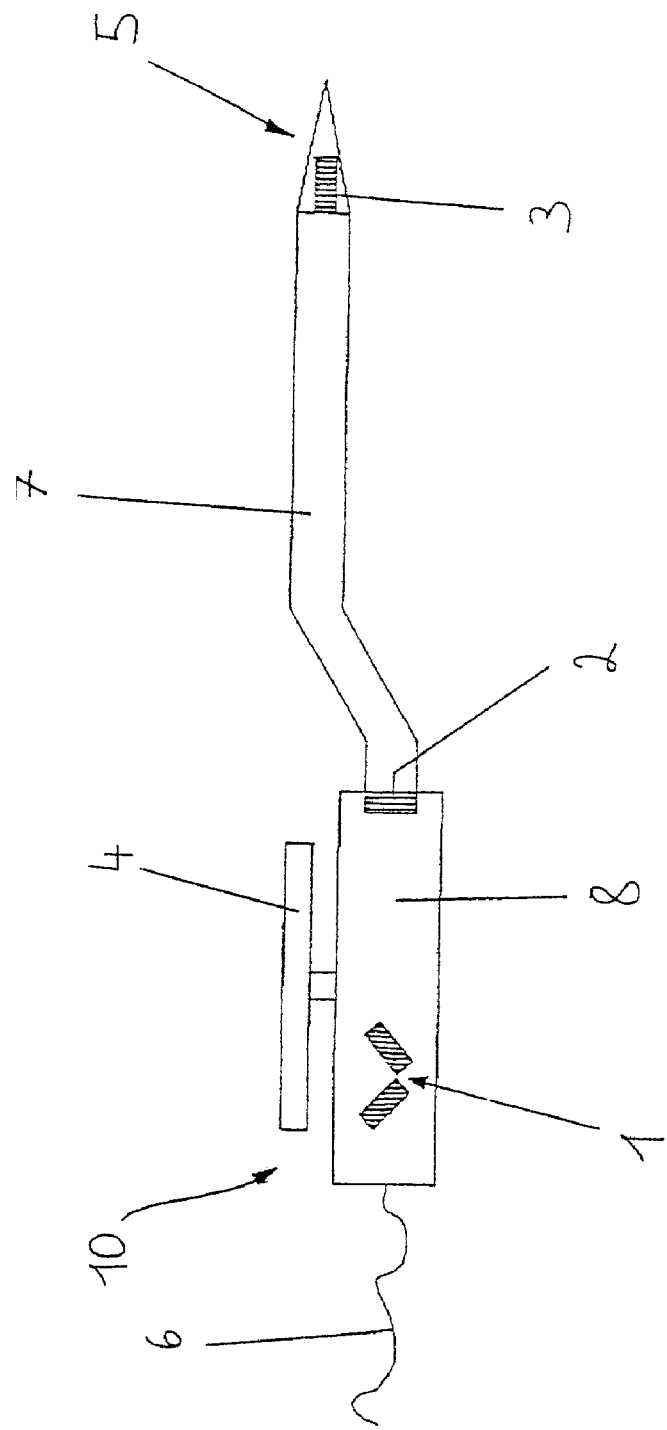

The invention relates to a medical instrument comprising an instrument body, an instrument tip and a tracking means which allows the spatial position of the instrument to be determined by means of a navigation means. Such medical instrument are currently used, for example, in a design as an indicator device or "pointer", to move to particular points of a patient or markers attached to the patient with the tip, in order to spatially register these points or markers by means of a navigation system. The navigation system thus also knows the position of the marker, because it knows the position of the instrument or pointer itself from the tracking means on the instrument, after the marker has for example been touched with the tip of the instrument, and by moving to a number of markers, the current position of the patient and that of the part of the body to be treated can be registered. Such a registering system is known for example from DE 19 639 615 C2. This has the disadvantage on the one hand that the navigation system always has to be informed that a marker has just been moved to for registration by a separate action, for example by an input at the navigation system. On the other hand, the marker may be shifted when touched by the tip of the pointer, such that inaccuracies may arise.

Another known referencing system does not use pointers, but rather shines points of light onto the surface of the patient's skin, the outer contours of which have been recorded beforehand using an image detection technique, for example CT or MR. The reflections on the surface of the patient's skin of a number of points of light are three-dimensionally detected by a camera system, from which a contour is calculated which is then assigned to the corresponding contour from image detection by so-called "surface matching". The current position of the patient in the navigation system can also be determined in this way. The disadvantage of this technique is that it can only be used with navigation systems which comprise optical position detection, for example using cameras. In recent times, however, navigation and/or tracking systems are increasingly being used which are based on magnetic detection, i.e. which track instruments in the range of an established magnetic field, wherein coils are arranged in the instruments whose position can be detected in the magnetic field. The non-contact technique mentioned above involving shining points of light cannot be used with such systems, since no camera system is available to detect the light reflections. It is therefore necessary to fall back on a system in which a number of points on the surface of the patient are moved to by means of a pointer tip, in order to then assign contours from the partial contour thus acquired, using surface matching. However, relatively large inaccuracies arise precisely when points are moved to on the surface of the skin by pointer tips, since the surface of the skin is very pliable and "dented in" points are often detected when the navigation system is informed—after a point on the surface of the skin has been moved to—that a point has been registered precisely at that moment (for example, by pressing a button on the instrument, or an input key of the navigation system). Conventional techniques thus lead to inaccuracies on the one hand, and are complicated to operate on the other.

It is the object of the present invention to provide a medical instrument which overcomes the above-cited disadvantages of the prior art. In particular, it should be made possible to precisely and simply detect the tip of the instrument touching an object.

This object is solved in accordance with the invention by a medical instrument comprising an instrument body, an instrument tip and a tracking means, wherein the instrument tip is fitted with a touch sensor which detects the tip touching an object. In other words, the instrument has a "tactile" tip by means of which it is possible to automatically detect whether said tip is touching an object or not.

One advantage of an instrument in accordance with the invention is that as soon as the tip touches an object, for example the surface of the patient's skin, this contact can be detected, i.e. still before the object itself is shifted by the contact. This substantially increases the detection accuracy. A further advantage is the fact that no separate protection is necessary on the part of the instrument operator, to inform a connected system of said contact; this can be done by the touch sensor itself, which results in very simple operation.

Another advantage is that a sensor may be selected which only generates a signal for particular object surfaces, such that false signals can be ruled out.

The medical instrument in accordance with the invention can comprise a transmission means which transmits a signal when contact is detected. In this respect, the touch sensor is operated as a touch switch, which in the event of contact outputs a signal. This signal can be transmitted to a connected system in various ways, i.e. for example, by a cable attached to the instrument or via a sender, for wirelessly transmitting the signal.

To avoid the touch sensor outputting signals constantly or in quick succession, it is advantageous to assign a control system to the transmission means or sensor, which only allows it to transmit another signal after a predetermined period of time has elapsed. Such an embodiment is important when, for example, an indicator device or pointer is fitted with a tactile tip in accordance with the invention. When said pointer is guided to a point on the surface of the patient's skin within the context of magnetic tracking registration, a signal is outputted as soon as the tip touches the surface of the skin, and before the skin can be dented by the instrument tip. Points are thus registered highly accurately. Using the signal transmission control system mentioned above, which only allows another transmission after a predetermined period of time has elapsed, registering signals are prevented from also being outputted while the surface of the skin is pressed in, which could distort overall registration.

Particularly advantageous is an embodiment of the instrument in accordance with the invention in which the tip may be removed from the instrument body. Such a removable tip can then be individually sterilized or kept sterile. In accordance with another embodiment, it is furthermore possible to design such tips the same as disposable articles, which could for example be packaged sterile and would not have to be sterilized again after use.

The tracking means, i.e. the device on the instrument which allows the latter to be tracked within a navigation system, can be a magnetic tracking means, wherein the instrument then comprises magnetic tracking coils. Such an embodiment is advantageous when no optical tracking system is available. However, the present invention can also be used in instruments comprising optical tracking means, i.e. arrangements of active or passive markings, for example; a combination is also conceivable.

The touch sensor can be an electrical resistance sensor, a capacity sensor or a mechanical sensor, and/or a combination of these types of sensor such as best corresponds to the application. In a preferred embodiment, the medical instrument is realized as an indicator device or pointer, in particular as a registering pointer for instrument tracking systems. The simple operation already mentioned above has an effect in this context in optical and magnet-based tracking systems, since separately operated switches on the instrument, foot switches or input switches on the navigation system no longer have to be operated. A registering pointer fitted in accordance with the invention has the particular advantage that it enables surface-matching registration without markings, even for magnetic tracking systems, and with high accuracy.

In the following, the invention will be explained in more detail by way of the enclosed drawing, which schematically shows a medical instrument in an embodiment as a registering pointer.

In the FIGURE, the pointer is indicated as a whole by the reference numeral 10. It comprises a base body 8, a front extension 7 and a tip 5. The pointer 10 shown can be used as a magnetic tracking pointer, and to this end it can be provided with small induction coils, as for example indicated at a number of points, i.e. at the pair of coils 1, in the instrument body 8, at the coil 2 at the transition point between the instrument body 8 and the extension 7, and directly in the tip 5 where the coil 3 is shown. The pair of coils 1 form a so-called "six-dimensional" sensor for magnetic tracking; the coils 2 and 3 each form a "five-dimensional" magnetic tracking sensor, and together a "six-dimensional" magnetic tracking sensor. The pair of coils 2, 3 alone suffice as a sensor unit, as does the pair of coils 1. Another optical tracking device, with the reference numeral 4, is also additionally shown in the drawing, and can be used as an alternative to or in combination with the magnetic tracking means. The optical tracking means 4 may consist for example of an arrangement of active or passive markers, i.e. of markers which emit light signals themselves, or of reflection markers.

A cable is indicated in the drawing by the reference numeral 6, via which a signal can be transmitted to a navigation system when the tactile tip 5 reports a contact. Though not shown, it is conceivable within the framework of the present invention to use a sender instead of the cable, said sender transmitting the contact signal wirelessly.

The tip 5 is a tactic tip, i.e. it comprises a touch-sensitive sensor, which may be any touch-sensitive sensor known in the technical field. Depending on the application, it can for example be an electrical resistance sensor, a capacity sensor or a mechanical sensor. The tip 5 works like a small, sensitive switch or electronic sensor capable of detecting surface contact. The sensor can incorporate the switch; however, the switch and the sensor can also be provided separately. The switch can also for example function mechanically or electrically and/or magnetically. Each time the pointer touches the surface of the object to be registered, i.e. for example a point on the surface of the skin, a signal—which can be digital or electrical—is generated or set. In a capacity sensor, for example, an alternating current flows via the patient, limited by capacitors to about 1 pF. The sensor then sets a signal level from "high" to "low", or vice versa.

In this way, the touch sensor can be used for highly accurate contour detection on the surface, since a point has always already been registered before the surface of the skin could be pressed in. A surface of the object and its spatial position can be determined from the spatial position of the pointer 10, which is obtained by the tracking means (the arrangement of coils and/or markers). No further, manual switch is necessary. When a sufficient number of points on the surface have been registered by contact, surface-matching allows registrating without markers, using the patient information obtained beforehand from image detection.

The invention claimed is:

1. A medical instrument comprising:
   an instrument body;
   an instrument tip; and
   a tracking device arranged in a known position relative to said instrument tip, said tracking device comprising an optical tracking device or a magnetic tracking device, wherein said instrument tip includes a touch-sensor which detects a contact between said tip and an object.

2. The instrument as set forth in claim 1, further comprising a transmission device which transmits a signal when contact is detected.

3. The instrument as set forth in claim 2, wherein said transmission device is a cable.

4. The instrument as set forth in claim 2, wherein said transmission device is a wireless transmission device for transmitting signals wirelessly.

5. The instrument as set forth in claim 2, wherein a control system is assigned to said transmission device and/or sensor, said control system only allowing the transmission device and/or sensor to transmit another signal after a predetermined period of time has elapsed.

6. The instrument as set forth in claim 1 wherein said tip is removable from said instrument body.

7. The instrument as set forth in claim 6, wherein said tip is disposable.

8. The instrument as set forth in claim 1, wherein said tracking device comprises magnetic tracking coils.

9. The instrument as set forth in claim 1, wherein said tracking device comprises an optically detectable arrangement of markers.

10. The instrument as set forth in claim 1, wherein said sensor is an electrical resistance sensor, a capacitance sensor, a mechanical sensor, or a combination of these types of sensors.

11. The instrument as set forth in claim 1, wherein the instrument is a registering pointer for instrument tracking systems.

* * * * *